(12) United States Patent
Karguth et al.

(10) Patent No.: US 11,452,571 B2
(45) Date of Patent: Sep. 27, 2022

(54) INSTRUMENT SUPPORT DEVICE FOR A MANIPULATOR OF A ROBOTIC SURGICAL SYSTEM

(71) Applicant: avateramedical GmbH, Jena (DE)

(72) Inventors: Andreas Karguth, Tuettleben (DE); Christian Trommer, Ilmenau (DE)

(73) Assignee: avateramedical GmbH, Jena (DE)

( * ) Notice: Subject to any disclaimer, the term of this patent is extended or adjusted under 35 U.S.C. 154(b) by 891 days.

(21) Appl. No.: 16/313,397

(22) PCT Filed: Jun. 14, 2017

(86) PCT No.: PCT/EP2017/064587
§ 371 (c)(1),
(2) Date: Dec. 26, 2018

(87) PCT Pub. No.: WO2018/001742
PCT Pub. Date: Jan. 4, 2018

(65) Prior Publication Data
US 2019/0159851 A1  May 30, 2019

(30) Foreign Application Priority Data

Jun. 27, 2016  (DE) .......................... 102016111737.4

(51) Int. Cl.
| | |
|---|---|
| *A61B 1/00* | (2006.01) |
| *A61B 34/30* | (2016.01) |
| *A61B 90/50* | (2016.01) |
| *A61B 34/00* | (2016.01) |
| *A61B 17/00* | (2006.01) |

(52) U.S. Cl.
CPC .......... *A61B 34/30* (2016.02); *A61B 1/00149* (2013.01); *A61B 34/70* (2016.02);
(Continued)

(58) Field of Classification Search
CPC ..... A61B 34/30; A61B 1/00149; A61B 34/70; A61B 90/50; A61B 2017/00477;
(Continued)

(56) References Cited

U.S. PATENT DOCUMENTS

| | | | |
|---|---|---|---|
| 2006/0074406 A1* | 4/2006 | Cooper .................. | A61B 34/30 606/1 |
| 2007/0137371 A1* | 6/2007 | Devengenzo .......... | A61B 46/10 74/490.01 |

(Continued)

FOREIGN PATENT DOCUMENTS

| | | |
|---|---|---|
| DE | 10 2013 004 459 A1 | 6/2014 |
| DE | 10 2013 012 840 A1 | 2/2015 |

(Continued)

*Primary Examiner* — Timothy J Neal
*Assistant Examiner* — Sung Ham
(74) *Attorney, Agent, or Firm* — Christensen, Fonder, Dardi & Herbert PLLC

(57) ABSTRACT

An instrument support device for a manipulator of a robotic surgical system, comprising: an arm having first, second and third arm elements; an interface for connecting the first arm element to the manipulator via a rotational joint; a torsional joint connecting the first and second arm elements; a first rotational joint connecting the second and third arm elements; a sliding joint connecting the third arm element to an instrument mounting for receiving a surgical instrument with a longitudinal axis; and a controller with drives for moving the arm elements and instrument mounting. The instrument mounting is connected to the third arm element via a second rotational joint, the rotational axes of the first and second rotational joints lie parallel to each other, and the longitudinal axis is guidable through a pivot point on the rotational axis of the torsional joint in an extension from the second arm element, without constraint.

6 Claims, 8 Drawing Sheets

(52) U.S. Cl.
CPC .... *A61B 90/50* (2016.02); *A61B 2017/00477* (2013.01); *A61B 2034/301* (2016.02)

(58) Field of Classification Search
CPC ... A61B 2034/301; A61B 34/00; A61B 34/71; A61B 34/77; A61B 1/00147; A61B 1/0016; A61B 2034/302; A61B 2034/303; A61B 2034/304; A61B 2034/305
See application file for complete search history.

(56) References Cited

U.S. PATENT DOCUMENTS

| | | | |
|---|---|---|---|
| 2011/0071473 A1 | 3/2011 | Rogers et al. | |
| 2013/0144307 A1* | 6/2013 | Jeong .................... | A61B 34/37 606/130 |
| 2013/0325029 A1 | 12/2013 | Hourtash et al. | |
| 2013/0325031 A1* | 12/2013 | Schena ................. | A61B 34/70 606/130 |
| 2014/0180309 A1* | 6/2014 | Seeber ................... | A61B 90/11 606/130 |
| 2015/0005784 A2 | 1/2015 | Seeber et al. | |
| 2016/0184030 A1 | 6/2016 | Seeber et al. | |
| 2017/0020615 A1* | 1/2017 | Koenig ................. | A61B 34/72 |
| 2019/0069964 A1* | 3/2019 | Hagn ..................... | A61B 34/30 |

FOREIGN PATENT DOCUMENTS

| | | | | |
|---|---|---|---|---|
| DE | 102013012840 A1 * | 2/2015 | ............ | A61B 34/30 |
| EP | 2 332 484 A2 | 6/2011 | | |
| WO | WO 2009/120945 A1 | 10/2009 | | |
| WO | WO 2014/094716 A1 | 6/2014 | | |

* cited by examiner

INSTRUMENT SUPPORT DEVICE FOR A MANIPULATOR OF A ROBOTIC SURGICAL SYSTEM

PRIORITY CLAIM

The present application is a National Phase entry of PCT Application No. PCT/EP2017/064587, filed Jun. 14, 2017, which claims priority from German Patent Application No. 10 2016 111 737.4, filed Jun. 27, 2016, the disclosures of which are hereby incorporated by reference herein in their entirety.

FIELD OF THE INVENTION

The invention relates to an instrument support device for a manipulator of a robotic surgical system. This device comprises a three-element arm as an end piece of an open kinematic chain with a first, second and third arm element. Here, a manipulator is that part of a robotic system which can interact physically with its surroundings, i.e., the moving part of the system. As a rule, this is a multi-element system in which the individual elements—also referred to in the following for reasons of clarity as arm elements—are connected to each other via joints. Some of the elements serve for positioning the manipulator relative to other manipulators of the same robotic system such that they do not impede each other, and are also referred to in the following as adjusting devices. Others of the elements—here of the instrument support device—serve for positioning the tool on the object, thus, for example, for positioning a surgical instrument or an endoscope in the region of an opening in the patient's outer tissue, e.g., the abdominal wall, for a minimally-invasive operation. The arm elements are connected to each other as an open kinematic chain as it is not a further joint which is seated on the last element but the tool, and all the other elements are connected to each other in the manner of a chain. At the ends of each arm element within the chain is a joint, such that each arm element comprises two joints, and the arm elements are connected to other arm elements via the joints. A joint connects precisely two elements. The joints allow the elements restricted movement relative to each other corresponding to the degrees of freedom available to the joint, wherein several joints can be formed on one element. In addition, two elements can also be connected by more than one joint. The joints can either be active, i.e., motor-driven, or passive, i.e., free-moving.

The three-element arm mentioned at the beginning forms the part of the manipulator responsible for the positioning of the instrument. The instrument support device therefore comprises first of all an interface for connecting the first arm element to the manipulator, i.e., the adjusting device of the manipulator. This connection is produced via an interface rotational joint. By a rotational joint is meant a joint with a rotational axis in which the rotational axis forms a right angle with the axes of the two connected arm elements. The axis of an element lies in its longitudinal direction, i.e., along the direction in which the element connects two joints or, in the case of the end arm element, between open end and joint. In contrast to the rotational joint, in the case of a torsional joint, the rotational axis runs parallel to the axes of the two arm elements and, in the case of a revolver joint, the longitudinal axis of one of the elements runs parallel to the rotational axis, and the longitudinal axis of the other element—as a rule the output element—is at a right angle to the rotational axis. The interface rotational joint is a rotational joint in which the rotational axis therefore forms a right angle with the axes of the two connected elements. The first arm element is connected to the second arm element via a torsional joint. The second and the third arm elements are connected to each other via a first rotational joint, and the third arm element is connected to an instrument mounting which has the function of a fourth arm element and forms the actual end of the kinematic chain, by means of a sliding joint, i.e., the third arm element and instrument mounting are movable with respect to each other along a slide axis, which here coincides with the longitudinal axis of the third arm element. The instrument mounting serves for receiving a surgical instrument with an instrument longitudinal axis. The rotational axis of the first rotational joint lies perpendicular to the rotational axis of the torsional joint.

The concept of the instrument longitudinal axis is to be understood as follows: in the case of minimally-invasive surgery by means of a robotic system, the instruments required for the operation, for example forceps, scissors or needle holders, are guided via a shaft mechanism with instrument shafts. To observe the operation site inside the body, rod-shaped camera systems, endoscopes with endoscope shafts, are used. The instrument longitudinal axis therefore corresponds to the longitudinal axis of such usually cylindrical instrument or endoscope shafts.

Finally, the instrument support device also comprises a controller with drives for the torsional joint, the first rotational joint and the sliding joint for moving the arm elements and the instrument mounting relative to each other. These joints are therefore active joints. By a joint which is also referred to as linear joint, translational joint or prismatic joint is meant a joint which brings about a sliding or advancing movement along the longitudinal axis of one arm element.

In the case of minimally-invasive surgery by means of robotic surgical systems, the conventional manual guidance of the instruments suitable for the minimally-invasive surgery is replaced by motorized positioning, wherein the positioning and the operation are carried out by hand by a surgeon. In the case of operations inside the body, the instrument shafts—in the following also referred to collectively as instrument—are guided inside the patient via one or more trocars. By a trocar is meant an instrument which the surgeon uses in the minimally-invasive surgical technique to gain access to a body cavity, such as for example the abdomen; the trocar usually has cutting edges for the sharp preparation of an access or a blunt conical tip for the blunt preparation. The cutting edges or the tip form the front end of a pin which sits in a tube; the tip of the trocar seals the opening of the tube. The tube is introduced together with the trocar into the corresponding body cavity, the trocar is then withdrawn from the tube and only the tube, through which the instrument shafts are guided, remains in the body. In the following, the term trocar is also intended to mean in particular the tube thereof, which is essential for positioning the surgical instrument, if it is used.

In principle, the surgical instrument can be moved and positioned as desired in all three spatial directions using the manipulator, however, the instruments—with or without the tube—are usually guided such that no or only minimal lateral movements of the instrument shafts can be performed at a point in the outer tissue. This point is referred to as pivot point, pivotal point or center of rotation. The control logic of the robotic surgical system must know the pivot point, or the pivot point must be defined by the constructional design of the movement mechanics in order to limit the movement of the instrument such that the biomechanical stress on the tissue around the tube or the penetration point through the tissue is as low as possible. At the pivot point, which ideally lies at the point where the trocar penetrates the patient's outer tissue or near this penetration point, lateral movements parallel to the surface of the outer tissue must be ruled out by design and/or control means in order to prevent injury to the outer tissue. At this point, the instrument shafts may therefore only be pivoted about the normal of the outer tissue and displaced in the direction of the normal, in addition to a rotation about the instrument longitudinal axis for orientation of the instrument.

BACKGROUND OF THE INVENTION

Various instrument support devices and corresponding manipulators with instrument supports for robotic surgical systems are known in the state of the art. In EP 2 332 484 A2 a manipulation unit for minimally-invasive surgery is described, which comprises a multi-element arm, on the end of which sits an instrument mounting which can be displaced by means of a sliding joint—also referred to as linear joint—along an instrument longitudinal axis in the vertical direction. This is connected via a rotational joint to a further arm element which is in turn connected via a torsional joint to another arm element. Here, the axis of the instrument mounting coincides with the instrument longitudinal axis or runs parallel thereto; the linear joint displaces the instrument mounting along its longitudinal axis. In order to suppress lateral forces perpendicular to the instrument longitudinal axis or in the outer tissue at the pivot point, complex compensating movements of the whole arm are necessary to adjust the instrument for a pivot movement, in order to hold the instrument at the predetermined position in the outer tissue. When several manipulators are used there is insufficient freedom of movement available in some circumstances such that collisions between the manipulators can occur. The location of the pivot point is always absolutely specified through the active coupling between instrument holder or trocar and manipulator.

These disadvantages are partially eliminated by a device described in WO 2014/094716. Here, the instrument longitudinal axis is decoupled from the axis along which a telescopic adjustment is effected, whereby the space necessary for the movement for positioning the instrument is reduced and the danger of collisions is minimized. For adjustment, on the one hand a telescopic guide with a cable-pull mechanism is used and on the other hand a coupling mechanism with six bearing points, i.e., a double coupling mechanism. In particular, the double coupling mechanism has a complicated construction and is therefore relatively prone to failure. Moreover, together with the telescopic guide, the space required is quite large.

SUMMARY OF THE INVENTION

The object of the invention is therefore to further develop an instrument support device of the type described at the beginning so that is firstly constructed as robustly as possible, i.e., less prone to failure, and secondly is as small as possible in order to increase maneuverability and, in association with other manipulators, when moving the manipulators to adjust a surgical position etc., the danger of collision is also minimized, with the result that greater freedom for the adjustment is obtained.

This object is achieved in the case of an instrument support device of the type described at the beginning in that the instrument mounting is connected to the third arm element not only via the sliding joint but also via a second passive rotational joint, about the axis of which the instrument mounting is freely rotatable, i.e., the movement about this joint is not controlled by a drive. The rotational axes of the first and of the second rotational joints lie parallel to each other. The second rotational joint is preferably located between the sliding joint and the instrument mounting, and can therefore be attached, for example, to a corresponding slide to which the instrument mounting is coupled and which shifts the instrument mounting. In principle it is also possible, but more complex in terms of construction, first of all to provide the second passive rotational joint on the third arm element and to couple the sliding joint to the instrument mounting thereon; the same kinematics are achieved in the end. What is important is that the third arm element is coupled to the instrument mounting not only via the sliding joint but also via the second passive rotational joint, i.e., therefore via two joints. In this way, the instrument longitudinal axis can be guided by a pivot point, which lies on the rotational axis of the torsional joint in an extension from the second arm element, without exerting a force. In contrast to the state of the art, the pivot point therefore lies not on the longitudinal axis or on an extension of the longitudinal axis of the third arm element, but offset on the rotational axis of the torsional joint, but outside the second arm element and the first rotational joint, i.e., on an extension of the rotational axis of the torsional joint. While, during an adjustment of the instrument support device, a longitudinal offset is also compensated for via the axis of the sliding joint, i.e., the axis of the displacement, the second rotational joint serves to make possible guidance of the instrument—i.e., of the instrument shaft—in the pivot point without constraint, i.e., without the instrument wanting to change its location in the plane which is defined by the tissue around the body opening, and only performing pivot movements about the pivot point. On the outer tissue, for example the abdominal wall of a patient, no lateral forces are exerted in this plane in the region of the opening. During operation, the instrument, i.e., the instrument longitudinal axis, is guided by this pivot point. Apart from the pivot movement, movements of the instrument along the instrument longitudinal axis as well as rotations about the instrument longitudinal axis are also possible, of course.

While, in the instrument support devices known in the state of the art, the instrument is always forcibly guided about the pivot point by the specific kinematics of the double coupling drive, which can lead to considerable tissue stresses in the case of incorrect system set-up, in the case of patients with very thick tissue layers, for example on the abdomen, or in the case of interim displacements of the patient, with the instrument support device according to the invention changes in position of the pivot point, i.e., of the point at which the instrument passes through the tissue, are compensated for passively and/or elastically.

In principle, no special device is necessary for the guidance of the instrument, i.e., of the instrument shaft; the body opening, possibly with an inserted tube of a trocar, is sufficient as supporting point and guidance when the location of the outer tissue and of the opening therein permits it to be used for the definition of the pivot point. In cases where it is not possible to produce such a pivotal point by means of the outer tissue of the patient's body, it is advantageous to realize the pivot point mechanically in another way. For this purpose, arranged on the second arm element in the region of the first rotational joint along the extension of the rotational axis of the torsional joint is a trocar holder which is formed for the pivotable mounting of a trocar about a pivot axis parallel to the rotational axis of the first rotational joint. The mounting can, for example, be forked and the tube of the trocar can be clamped into this mounting or pivotably screwed thereto, to name but two possible examples for producing the mounting. The pivot point is then the intersection of the rotational axis of the torsional joint with the pivot axis. The use of a trocar holder is advantageous in particular when, for example, open operations are to be carried out in which no outer tissue with which a pivot point could be defined is available. The trocar holder can, moreover, also be used as target-guide in order, for example, to set up the instrument support device for basic positioning in relation to the patient without a trocar being used during the operation.

Instead of the double coupling known in the state of the art, a sliding joint is used here in combination with a free rotational joint; the sliding joint can be designed, for example, as a linear guide with belt and/or spindle drive, which makes possible a compact configuration and a design that is robust against external mechanical influences. The position of the sliding joint along a sliding joint axis, i.e., the axis along which the displacement takes place, can be determined advantageously by means of relative encoders and reference position encoders arranged along the sliding joint axis. In this way, the configuration can be kept particularly compact and, because various reference switches are arranged in the area in which the displacement takes place, the referencing after switching on can be reduced to a minimum.

Finally, the instrument mounting can be coupled to the third arm element or the sliding device thereof in various ways. For example, it can be a purely mechanical locking mechanism, which makes rapid replacement of the instrument mounting possible, for example, if two instruments have to be exchanged. Electrical or electromagnetic contacts for controlling the instrument can be integrated into this locking mechanism; however, the control signals can also be transmitted wirelessly.

It is understood that the features mentioned above and those yet to be explained below can be used not only in the stated combinations but also in other combinations or alone without departing from the scope of the present invention.

BRIEF DESCRIPTION OF THE DRAWINGS

The invention is explained in yet more detail below by way of example with reference to the attached drawings, which also disclose features essential to the invention. There are shown in.

DETAILED DESCRIPTION

Figure 1:
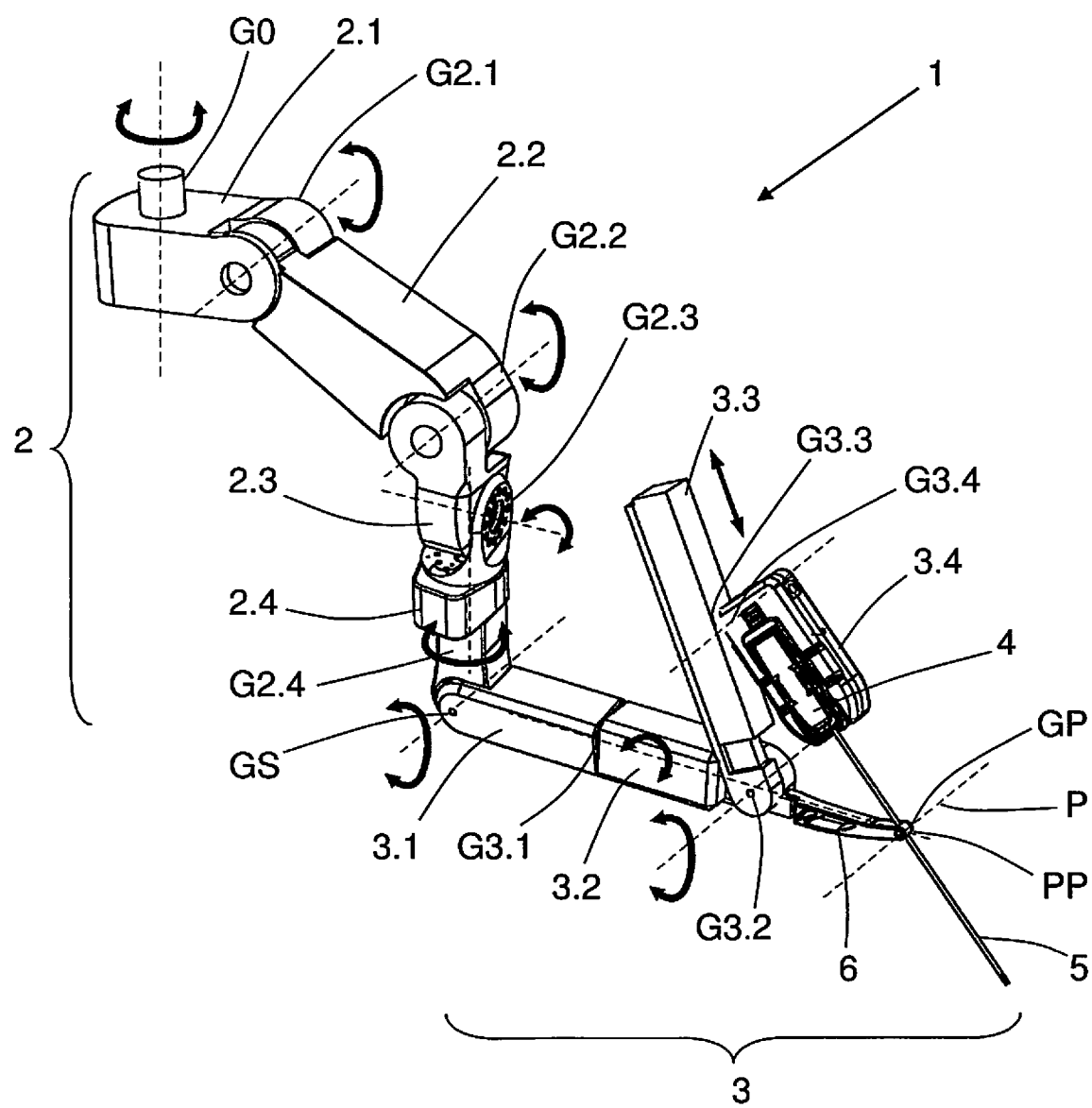
FIG. 1 a manipulator of a robotic surgical system in a general view.
Figure 2:
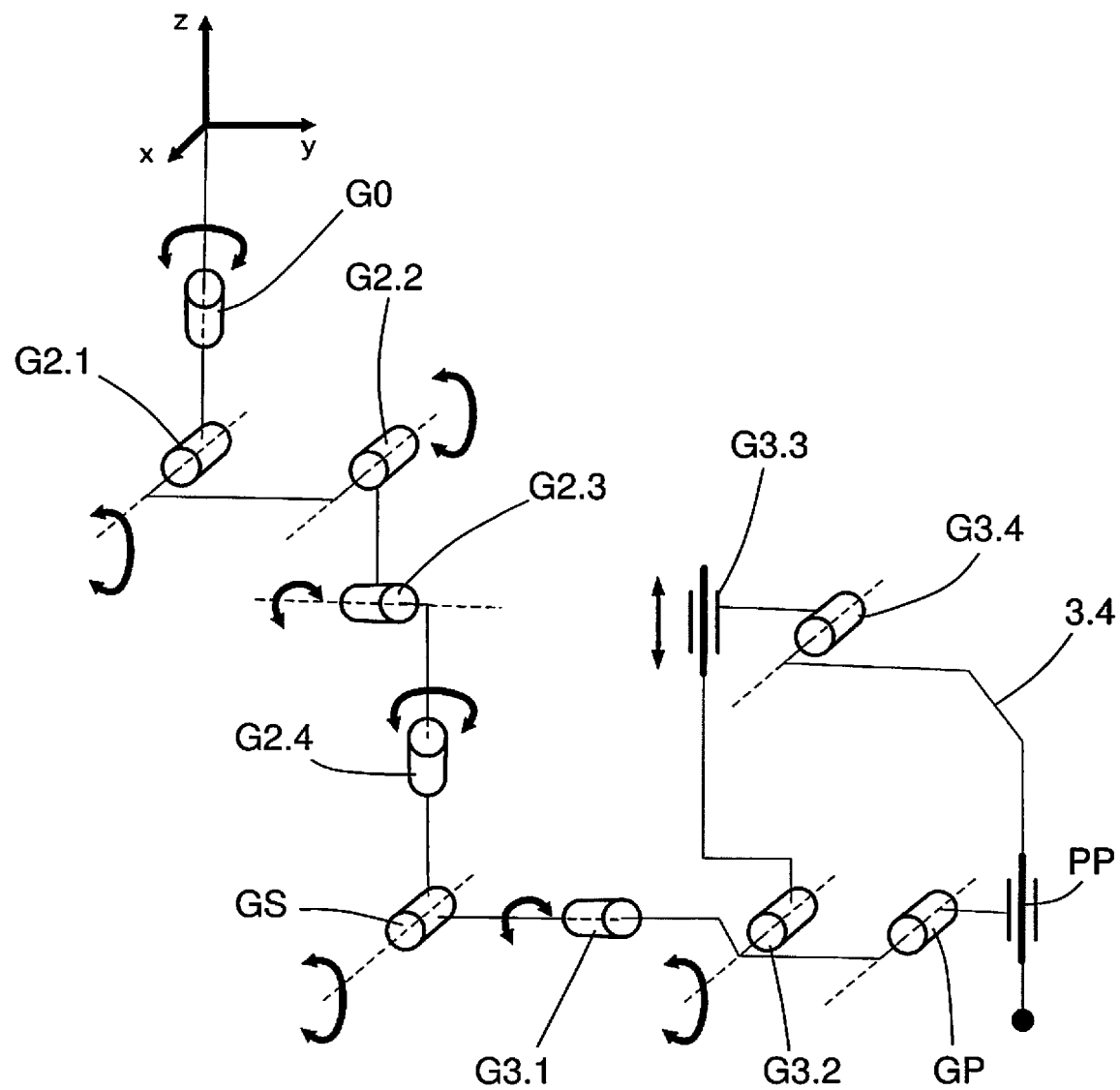
FIG. 2 the kinematics of this manipulator.

FIG. 1 shows a manipulator 1 of a robotic surgical system and FIG. 2 shows the kinematic relationships in the case of the manipulator 1. As a rule, a robotic surgical system comprises several manipulators, for example, four or six. The manipulator 1 consists of an adjusting device 2 and an instrument support device 3. The adjusting device 2 serves, in combination with the other manipulators, to position the instrument support device 3 such that the instrument support devices of the different manipulators do not impede each other during the operation. The position of the instrument is adjusted on the instrument support device 3 during and for the operation; during the operation the adjusting device 2 usually remains in its position. The adjusting device 2 consists of several adjusting arm elements 2.1, 2.2, 2.3 and 2.4. The adjusting arm element 2.1 is connected to the remaining, usually non-moving part, of the robotic surgical system via a rotational joint G0, wherein the complete system itself can optionally be movable. The elements of the adjusting device 2, the adjusting arm elements 2.1 to 2.4, can be moved with respect to each other via driven and actuated joints G2.1, G2.2, G2.3 and G2.4.

For its part, the instrument support device 3 comprises a three-element arm as end piece of an open kinematic chain with a first arm element 3.1, a second arm element 3.2 and a third arm element 3.3. The first, proximal arm element 3.1 is connected to the manipulator 1, that is the adjusting device 2 of the manipulator 1, via an interface. The electrical contacts for the controller are also laid through the interface, unless the controller is effected wirelessly. The interface also comprises an interface rotational joint GS, the rotational axis of which is thus perpendicular to the longitudinal axes of the first arm element 3.1 and of the adjusting arm element 2.4 arranged closest to the first arm element. The first arm element 3.1 of the instrument support device 3 is connected to the second arm element 3.2 via a torsional joint G3.1. The range of movement of the torsional joint G3.1 lies, for example, in a range of ±120°, preferably of ±100° around a dead-center position or rest position. The second arm element 3.2 is connected to the third, distal arm element 3.3 via a first rotational joint G3.2, the range of movement of which lies, for example, between −40° and +90°, preferably between −30° and +70° around a dead-center position or rest position. In the rest position of the torsional joint G3.1, the rotational axes of the interface rotational joint GS and of the first rotational joint G3.2 lie parallel. In the rest position of the first rotational joint, the third arm element 3.3 or the longitudinal axis thereof is perpendicular to the rotational axis of the torsional joint G3.1 and to the rotational axis of the first rotational joint G3.2. For its part, the third arm element 3.3 is connected via a sliding joint G3.3 to an instrument mounting 3.4. The instrument mounting 3.4 should be adjustable over a length range of at least 30 cm, preferably at least 44 cm, wherein this length range is scaled to the overall size of the surgical system; the above specification relates to systems for minimally-invasive interventions on the human body. The instrument mounting 3.4 serves to receive a surgical instrument which comprises an instrument head 4 and an instrument shaft 5. By a surgical instrument is also intended to be meant an endoscope, which is used during surgery for observation. The controller and part of the mechanism for the movement of the instrument parts are accommodated in the instrument head 4; as a rule, the instrument shaft 5 is introduced into the body through an artificially produced body opening in the patient's outer tissue, for example through the abdominal wall. The instrument shaft 5 at the same time defines an instrument longitudinal axis I—shown, for example, in the non-perspective drawings FIG. 5 and FIG. 7a—i.e., the instrument longitudinal axis I corresponds to the axis of symmetry of the instrument shaft 5, in the case, for example, of cylindrical shafts. By a surgical instrument is thus meant not only scissors, needles, etc., but also devices for observing the area to be operated on, such as for example endoscopes; a corresponding instrument mounting 3.4 for such an endoscope 18 with an endoscope shaft 19 is shown, for example, in FIGS. 7a, b.

The instrument support device 3 also has a controller (not shown) with drives for the torsional joint G3.1, the first rotational joint G3.2 and the sliding joint G3.3 for moving the three arm elements 3.1, 3.2 and 3.3 and the instrument mounting 3.4 relative to one another.

What is special about the instrument support device 3 shown is that the instrument mounting 3.4 is not connected to the third arm element 3.3 exclusively via the driven sliding joint G3.3 but additionally also via a second rotational joint G3.4. This second rotational joint G3.4 is a passive joint; therefore, it is not driven or moved by a controller but is in principle freely rotatable about the rotational axis of the joint within certain limits imposed by the construction. The range of movement or pivoting angle of the second rotational joint G3.4 is approximately ±9° about a central location, for example. The rotational axes of all the joints are indicated by dashed lines in FIG. 1 and FIG. 2; the possibilities for rotational and sliding movements in the case of the driven joints are indicated by corresponding double arrows. The instrument mounting 3.4 is therefore connected to the third arm element 3.3 via two joints, on the one hand via the sliding joint G3.3 and on the other hand via the second rotational joint G3.4.

The rotational axes of the first rotational joint G3.2 and of the second rotational joint G3.4 lie parallel to each other. In this way, the instrument longitudinal axis I, also represented by the instrument shaft 5, can be guided through a pivot point PP which does not lie in the first rotational joint G3.2 or on the longitudinal axis of the third arm element 3.3 but on the rotational axis of the torsional joint G3.1 in an extension from the second arm element 3.2, without constraint. The location of the instrument longitudinal axis I or of the instrument shaft 5 is therefore partially decoupled from the location of the longitudinal axis of the arm element 3.3 and the rotational axis of the first rotational joint G3.2 does not run through the pivot point PP. A longitudinal offset is compensated for via the sliding axis, i.e., the longitudinal axis of the arm element 3.3, and a force-free guidance of the instrument is possible through the free rotational movement between the instrument mounting 3.4 and the third arm element 3.3 through the second rotational joint G3.4. The instrument mounting 3.4, which could also be referred to as fourth arm element, is therefore connected to the third arm element via two joints, the sliding joint G3.3 and the second rotational joint G3.4. This design allows a compact configuration which additionally manages with few robustly constructible joints. This increases the stability of the whole surgical system. Since the pivot point PP does not lie directly in the instrument support device, fewer adjusting movements are necessary to realize the required positioning possibilities; the required space is smaller. In addition, the potential for collision with the other manipulators of the robotic surgical system is reduced to a minimum. The pivot point PP lies on the extension of the rotational axis of the torsional joint G3.1 clearly outside of the instrument support; typically, the minimum spacing between the instrument support device 3 and the pivot point PP along the rotational axis of the torsional joint G3.1 should be approximately 10 cm.

As a rule, no further aids are necessary to guide the instrument at the pivot point PP when the pivot point PP can be defined, for example, by a body opening in the outer tissue, such as the abdominal wall. During the operation, no lateral movement by the instrument shaft takes place in the plane defined by the abdominal wall or outer tissue. In situations where such a pivot point PP cannot be defined by a corresponding outer tissue it is advantageous if a trocar holder 6 is arranged on the second arm element 3.2 in the region of the first rotational joint G3.2 along the extension of the rotational axis of the torsional joint G3.1—indicated by the dashed line, which runs along the longitudinal axis of the first arm element 3.1 and of the second arm element 3.2 and on which the pivot point PP lies. This is formed for the pivotable mounting of a trocar about a pivot axis P parallel to the rotational axis of the first rotational joint G3.2. This trocar holder 6 can, for example, be plugged onto a corresponding adapter, which is formed on the end of the second arm element 3.2, and be fixed in the plugged-on position with a snap-on connection. Other connections are also conceivable, for example a plug-and-socket connection or a screw connection. The connection is force- and/or form-fitting. Here, the instrument shaft 5 is guided by a corresponding mounting on the pivot axis P; this mounting can consist of a form-fitting but not force-fitting holding of the instrument shaft 5 since the latter must be held displaceable along its longitudinal axis. For example, a free joint can be provided as pivot mounting GP, which has a through-hole through which the instrument shaft 5 can be guided.

The kinematic relationships are represented more precisely in FIG. 2. Driven joints are indicated by the corresponding double arrows. The second rotational joint G3.4, the pivot mounting GP and the guidance of the instrument shaft 5 through the pivot point PP are not driven; this movement is caused by the sliding joint G3.3 in combination with the second rotational joint G3.4.

Figure 3A:
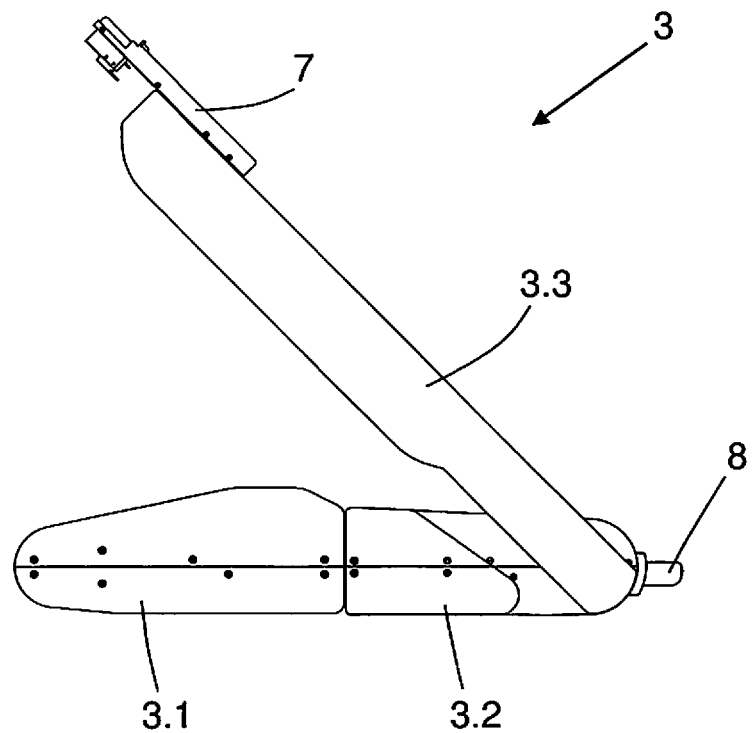
FIGS. 3a, b an instrument support device in two different positions from the side, FIGS. 4a, b an instrument support device from another side in two different positions, FIG. 5 an instrument support device with coupled-on instrument mounting, FIGS. 6a, b, c a further design of the instrument support device with instrument mounting, and FIGS. 7a, b an instrument support device with another instrument mounting.
Figure 3B:
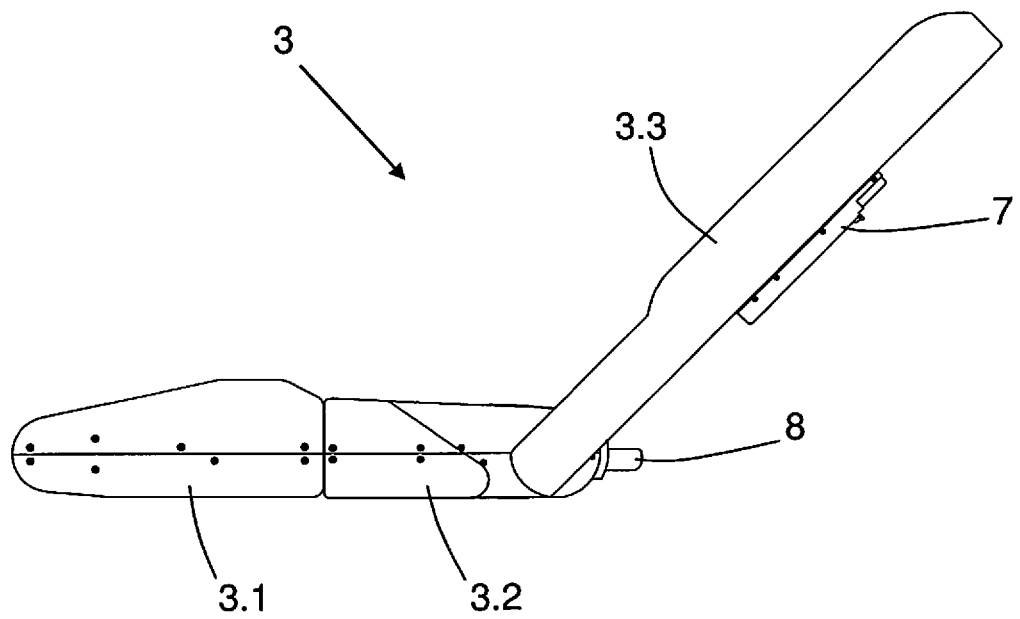

FIGS. 3a and 3b show an instrument support device 3, but without instrument mounting 3.4, in two different positions of the third arm element 3.3. In FIG. 3a a negative displacement of the first rotational joint G3.2 is shown and in FIG. 3b a positive displacement. Pivoting of the third arm element 3.3 is accompanied by an adjustment of the sliding joint G3.3; this sliding joint G3.3 guides a slide 7 on which the instrument mounting 3.4 can be arranged or to which it can be connected. The second rotational joint G3.2 is not formed on the slide 7 but on the instrument mounting 3.4; however, in a design modification, it can also be readily formed on the slide 7. In the continuation of the second arm element 3.2 on the side facing away from the first arm element 3.1, an adapter 8 for connection to the trocar holder 6 is also represented.

Figure 4A:
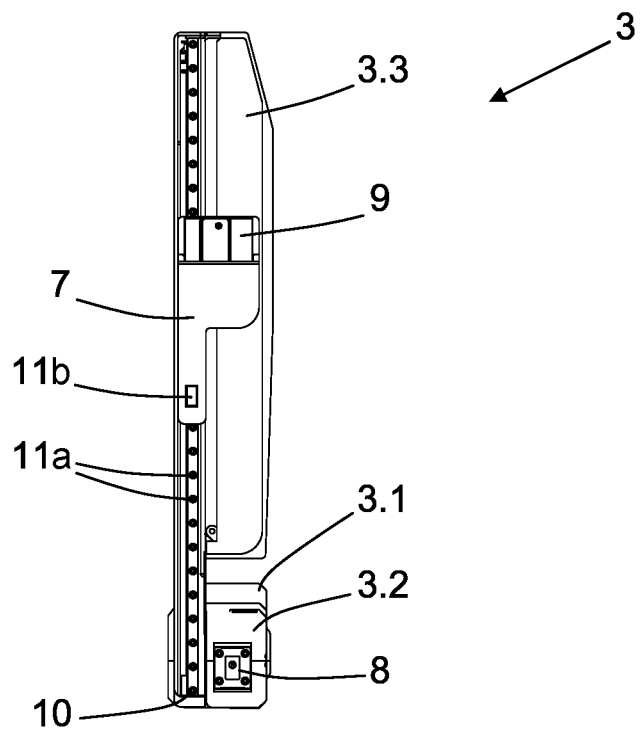
Figure 4B:
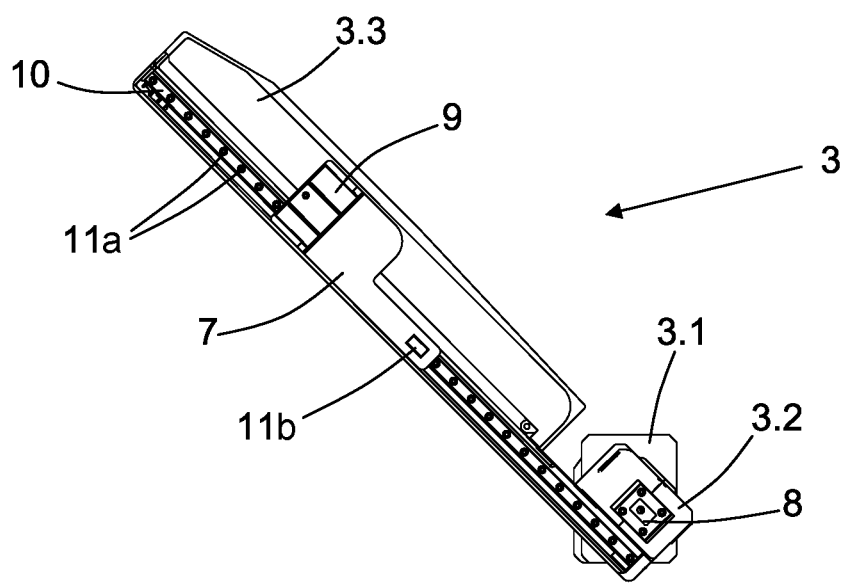

FIGS. 4a and 4b show the instrument support device 3 in another view in which the arm element 3.3 is represented in detail. In FIG. 4a, the torsional joint G3.1 and thus the second arm element 3.2 are in the rest position—also referred to as dead-center position—relative to a torsion with respect to the first arm element 3.1, i.e., the rotational axes of the interface rotational joint GS and of the first rotational joint G3.2 lie parallel. In FIG. 4b, the second arm element 3.2 is in a different position compared with the position in FIG. 4a, thus also the third arm element 3.3 that has not moved with respect to the second arm element 3.2. A representation of the instrument mounting 3.4 has also been dispensed with here. The sliding joint is preferably designed as linear guide 10 with spindle drive and/or belt drive; this design is very robust. The position of the slide 7 along a sliding joint axis—corresponding to the longitudinal axis of the third arm element 3.3 and parallel to the linear guide 10—can be determined by means of relative encoders 11b; reference position encoders 11a are arranged along the sliding joint axis for this purpose. The slide 7 is moved in the linear guide 10 along the longitudinal extension of the third arm element 3.3 by the drive. An instrument coupling 9 is also located on the slide 7; the instrument mounting 3.4 can be coupled on here.

Figure 5:
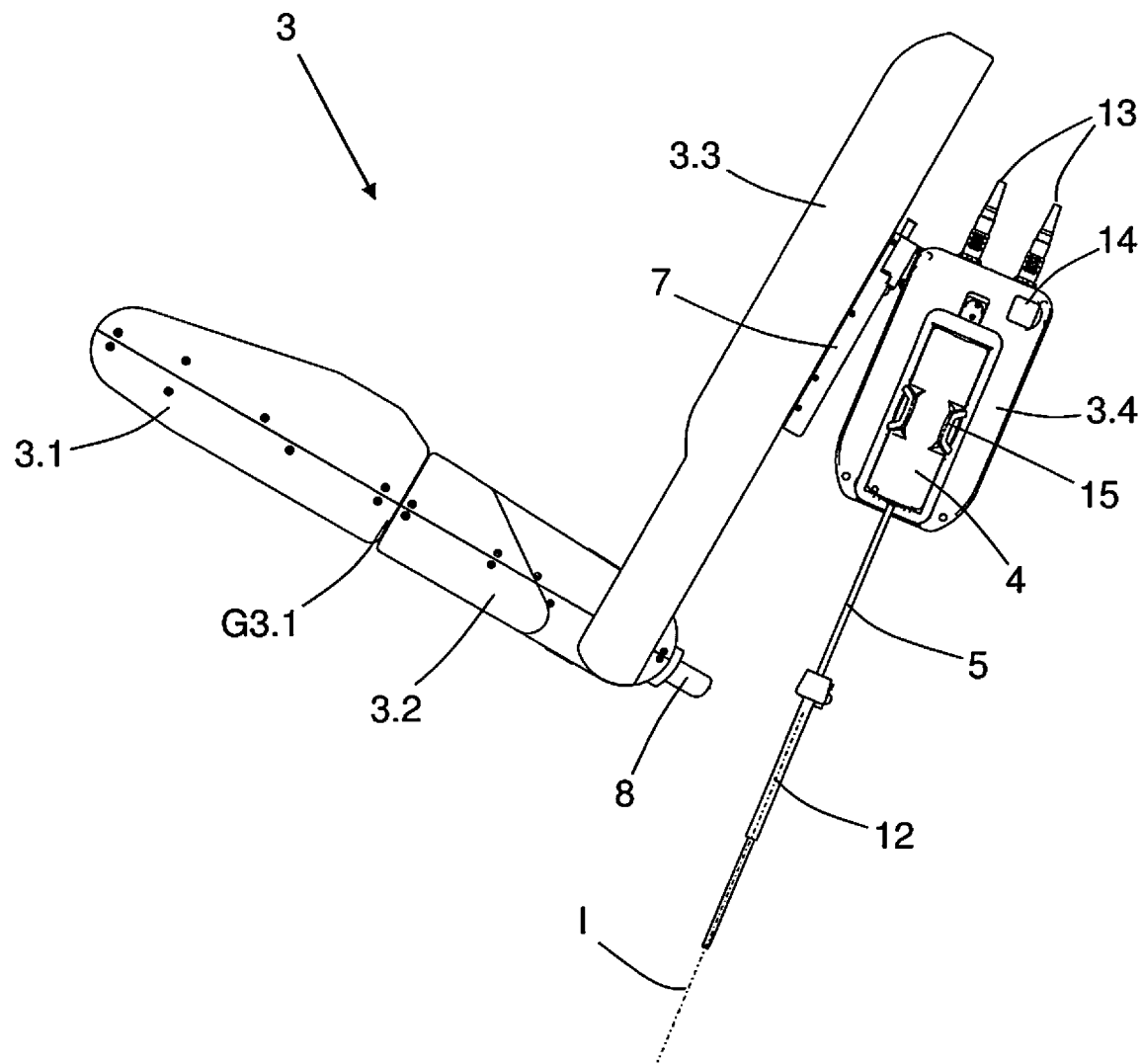

An instrument support device 3 with a coupled-on instrument mounting 3.4 and an instrument received therein is represented in FIG. 5. The third arm element 3.3 or the first rotational joint G3.2 are in the rest position here. The instrument shaft 5 is guided through a trocar, more precisely through the tube 12 of a trocar. This is introduced into the outer tissue. The adapter 8 is not required in this case. The control signals for the instrument are transmitted via antennae 13; for this purpose, small transmitters for transmitting signals wirelessly can be arranged on the slide 7. The wireless transmission of the signals is advantageous since otherwise wires would have to be used, the mechanical stability of which can be stressed by pivoting about the rotational axis of the second rotational joint G3.4 and which can be easily worn. A pushbutton 14 is also arranged on the instrument mounting 3.4. This can be designed, for example, as a mechanical pushbutton, in order to release the instrument head 4 from the instrument mounting 3.4, which is here held in position by a locking mechanism 15, or also in order to release the motor brake and to make possible a manual operation of the slide 7, if the instrument is to be exchanged or removed, for example. The instrument longitudinal axis I corresponds to the axis of symmetry of the instrument shaft 5 of the surgical instrument.

The instrument mounting 3.4 can also be connected to the third arm element 3.3 by means of a locking mechanism; this enables a simple and rapid assembly and disassembly. Other connections are also possible, for example a screw connection.

Figure 6A:
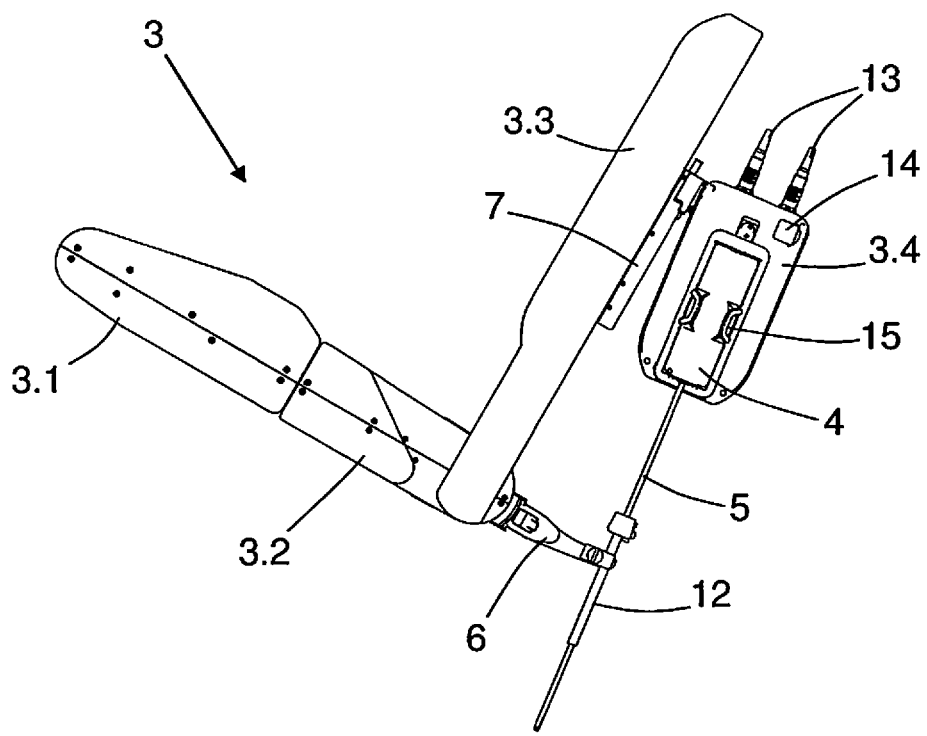
Figure 6B:
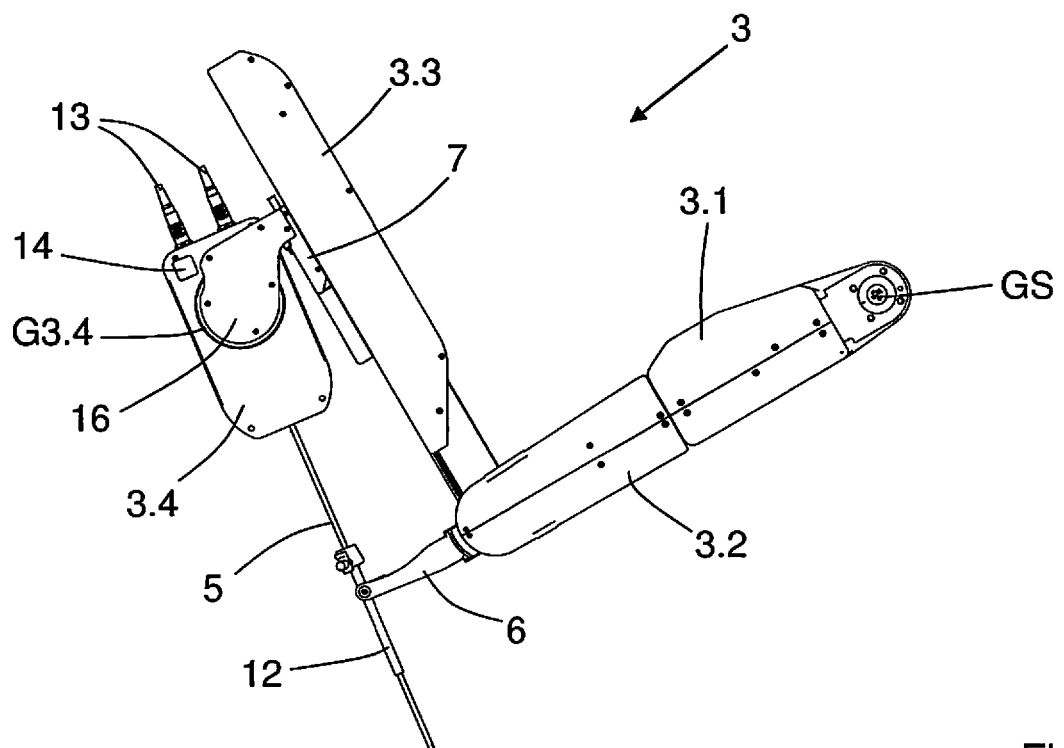
Figure 6C:
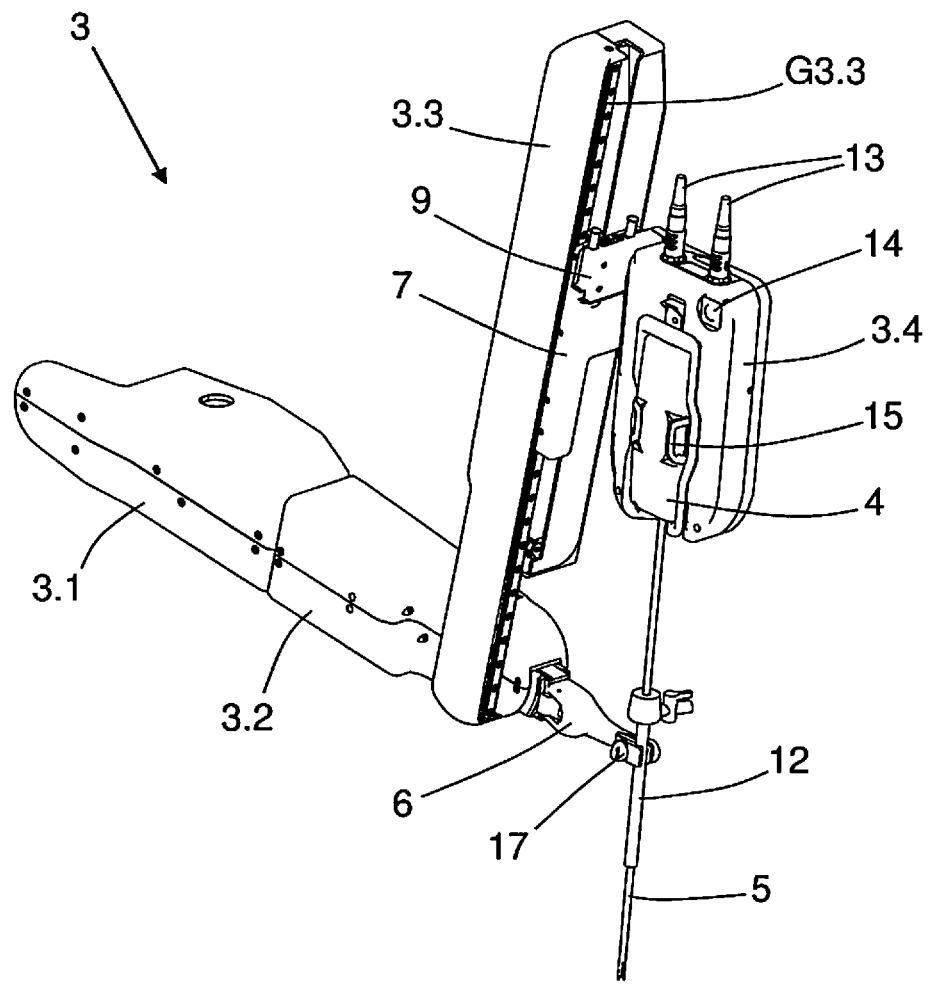

While no trocar holder 6 is used in the embodiment shown in FIG. 5, this is the case in the embodiment shown in FIGS. 6a and 6b. FIGS. 6a and 6b show an instrument support device 3 from two opposite viewing directions; the rear side of the instrument mounting 3.4 is represented in FIG. 6b. A further pushbutton 14, which can have a different function from the pushbutton 14 on the front side, is also located on the rear side. However, it can also be coupled to the pushbutton 14 on the front side, with the result that, for example, only by pressing on both pushbuttons 14 together does the locking mechanism open and release the instrument head, or the motor brake is released. The instrument mounting 3.4 is connected to the slide 7 via the joint G3.4 and a joint holder 16. FIG. 6c shows the instrument support device 3 shown in FIGS. 6a and 6b in a perspective view. Here, the tube 12 is pivotably fixed in a clamping device 17 formed on the trocar holder 6.

Figure 7A:
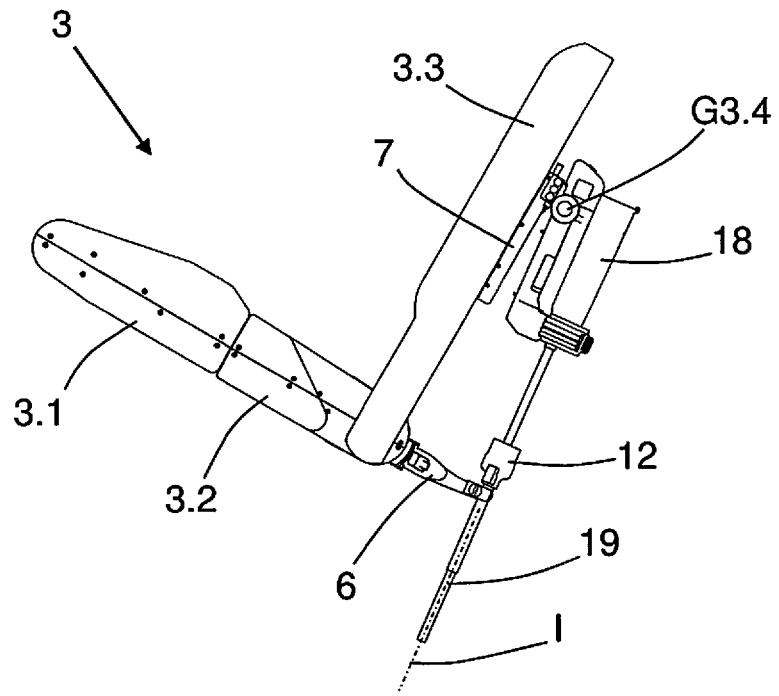
Figure 7B:
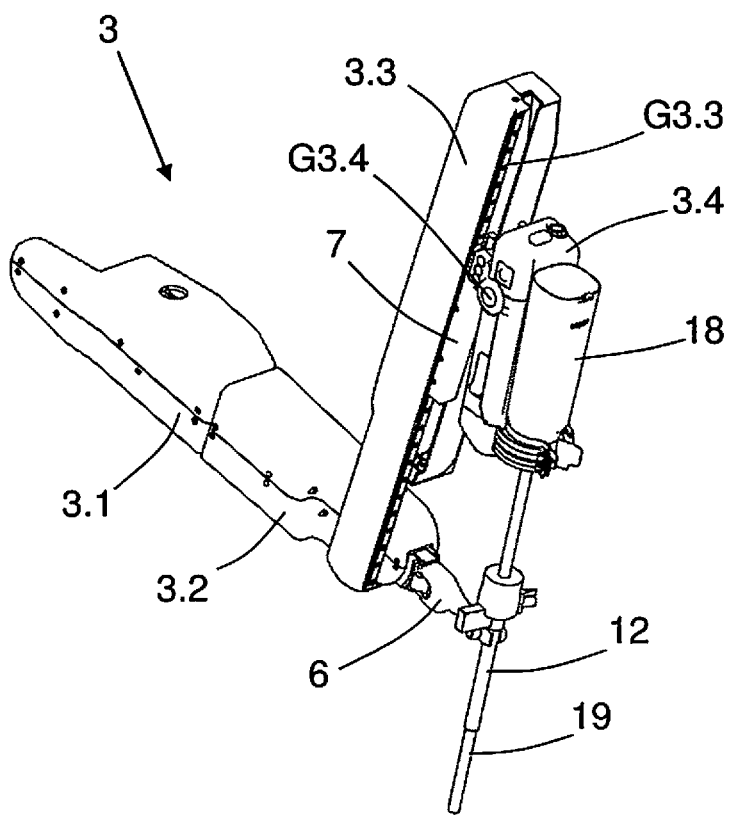

Finally, FIGS. 7a, 7b show an instrument support device 3 with another instrument mounting 3.4, to which is coupled an endoscope 18 with an endoscope shaft 19. This configuration of the instrument mounting 3.4, which is also suitable for other surgical instruments, requires less space since the joint can be better integrated into the instrument mounting 3.4 due to the arrangement rotated by 90° compared with the design shown in FIG. 6. The endoscope 18 also has an instrument longitudinal axis I which corresponds to the axis of symmetry of the endoscope shaft 19.

The device described above makes it possible to construct in a compact and robust manner a robotic surgical system, in particular a manipulator for a robotic surgical system, which facilitates conditioning of the surgical system by the operator, the surgeon, and reduces the pressure for the patient due to the force-free mounting of the instrument or trocar at the pivot point.

LIST OF REFERENCE NUMBERS

1 manipulator
2 adjusting device
2.1-2.4 adjusting arm elements
3 instrument support device
3.1-3.3 arm element
3.4 instrument mounting
4 instrument head
5 instrument shaft
6 trocar holder
7 slide
8 adapter
9 instrument coupling
10 linear guide
11 reference position encoder
12 tube
13 antenna
14 pushbutton
15 locking mechanism
16 joint holder
17 clamping device
18 endoscope
19 endoscope shaft
GP pivot mounting
GS interface rotational joint
G0 holding joint
G2.1-G2.4 adjusting device joint
G3.1 torsional joint
G3.2 first rotational joint
G3.3 sliding joint
G3.4 second rotational joint
I instrument longitudinal axis
PP pivot point

The invention claimed is:

1. An instrument support device for a manipulator of a robotic surgical system, comprising:
   a three-element arm as end piece of an open kinematic chain with a first, second and third arm element;
   an interface for connecting the first arm element to the manipulator via an interface rotational joint;
   a torsional joint which connects the first arm element to the second arm element;
   a first rotational joint which connects the second arm element to the third arm element;
   a sliding joint which connects the third arm element to an instrument mounting for receiving a surgical instrument with an instrument longitudinal axis; and
   a controller with drives for the torsional joint, the first rotational joint and the sliding joint for moving the first, second and third arm elements and the instrument mounting relative to one another;
   wherein, the instrument mounting is connected to the third arm element via a second, passive rotational joint and is freely rotatable about a rotational axis thereof, and rotational axes of the first rotational joint and of the second rotational joint lie parallel to each other, whereby the instrument longitudinal axis is guidable through a pivot point, which lies on the rotational axis of the torsional joint in an extension from the second arm element, without constraint.

2. The instrument support device according to claim 1, wherein, arranged on the second arm element in the region of the first rotational joint along the extension of the rotational axis of the torsional joint, is a trocar holder which is formed for the pivotable mounting of a trocar about a pivot axis parallel to the rotational axis of the first rotational joint.

3. The instrument support device according to claim 1, wherein the sliding joint is designed as a linear guide with a spindle drive.

4. The instrument support device according to claim 1, further comprising relative encoders in addition to reference position encoders arranged along the sliding joint axis configured to determine a position of the sliding joint along a sliding joint axis.

5. The instrument support device according to claim 1, wherein the instrument mounting can be connected to the third arm element via a locking mechanism located at a joint holder that is coupled to the instrument mounting.

6. The instrument support device according to claim 1, wherein an endoscope with an endoscope shaft is coupled to the instrument mounting.

\* \* \* \* \*